United States Patent

Stubbs et al.

(10) Patent No.: US 10,106,754 B2
(45) Date of Patent: Oct. 23, 2018

(54) METHOD OF MARKING HYDROCARBON LIQUIDS

(71) Applicant: JOHNSON MATTHEY PUBLIC LIMITED COMPANY, London (GB)

(72) Inventors: David Stubbs, Cleveland (GB); Duncan William John McCallien, County Durham (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/590,145

(22) Filed: May 9, 2017

(65) Prior Publication Data

US 2017/0240826 A1  Aug. 24, 2017

Related U.S. Application Data

(63) Continuation of application No. 14/116,668, filed as application No. PCT/GB2012/051015 on May 9, 2012, now Pat. No. 9,678,054.

(30) Foreign Application Priority Data

May 11, 2011  (GB) .................................. 1107870.6

(51) Int. Cl.
    C10L 1/00    (2006.01)
    C10L 1/20    (2006.01)
    C10L 1/16    (2006.01)

(52) U.S. Cl.
    CPC ................. *C10L 1/003* (2013.01); *C10L 1/16* (2013.01); *C10L 1/201* (2013.01); *C10L 1/202* (2013.01); *C10L 2230/16* (2013.01)

(58) Field of Classification Search
    CPC ........ G01N 33/2882; C10L 1/003; C10L 1/16
    See application file for complete search history.

(56) References Cited

U.S. PATENT DOCUMENTS

| | | | |
|---|---|---|---|
| 3,817,721 A | 6/1974 | Warren | |
| 4,141,692 A | 2/1979 | Keller | |
| 4,231,426 A * | 11/1980 | Carter | C09K 8/58 166/252.6 |
| 4,501,324 A | 2/1985 | Sandiford et al. | |
| 5,474,937 A * | 12/1995 | Anderson, II | C06B 23/008 436/139 |
| 2006/0052251 A1 * | 3/2006 | Anderson | E21B 47/1015 507/103 |

FOREIGN PATENT DOCUMENTS

| | | |
|---|---|---|
| EP | 1580254 A2 | 9/2005 |
| GB | 919184 | 9/1959 |
| GB | 998520 | 5/1963 |
| GB | 2172302 | 9/1986 |
| WO | 2006047091 | 5/2006 |
| WO | 2011032857 | 3/2011 |

OTHER PUBLICATIONS

International Search Report, dated Aug. 2, 2012, from corresponding PCT application.
United Kingdom Search Report, dated Sep. 9, 2011, from corresponding United Kingdom application.

\* cited by examiner

*Primary Examiner* — Krishnan S Menon
*Assistant Examiner* — Dwan A Gerido
(74) *Attorney, Agent, or Firm* — Baker & Hostetler LLP

(57) ABSTRACT

Method of marking a hydrocarbon liquid includes adding to the liquid, a tracer compound of Formula I or II:

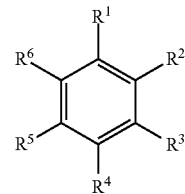

Formula I

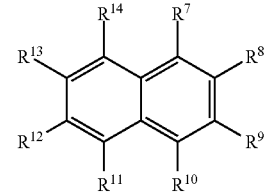

Formula II wherein at least one of $R^1$-$R^6$ in Formula I and at least one of $R^7$-$R^{14}$ in Formula II is selected from:
  i. a bromine or fluorine atom;
  ii. a partially or fully halogenated alkyl group;
  iii. a branched or cyclic $C_4$-$C_{20}$ alkyl group;
  iv. an aliphatic substituent linking two positions selected from $R^1$-$R^6$ in Formula I to one another or two positions selected from $R^7$-$R^{14}$ in Formula II to one another; or
  v. a phenyl group substituted with a halogen atom, an aliphatic group or halogenated aliphatic group
and none of $R^1$-$R^6$ and none of $R^7$-$R^{14}$ being a sulphonate group or $COOR^{15}$, where $R^{15}$ represents H, $C_1$-$C_{20}$ alkyl, $C_2$-$C_{20}$ alkenyl, $C_2$-$C_{20}$ alkynyl, $C_3$-$C_{15}$ cycloalkyl or aryl.

12 Claims, No Drawings

METHOD OF MARKING HYDROCARBON LIQUIDS

The present invention concerns marking hydrocarbon liquids with tracer materials for identification purposes, in particular hydrocarbons which are taxable or liable to be subject to tampering or substitution such as gasoline and diesel fuels for example.

It is well known to add tracers to hydrocarbon liquids. A typical application is the tagging of hydrocarbon fuels in order to identify the liquid at a subsequent point in the supply chain. This may be done for operational reasons, e.g. to assist in distinguishing one grade of fuel from another, or for other reasons, in particular to ensure fuel quality, deter and detect adulteration and to provide a means to check that the correct tax has been paid. Apart from fuels, other products, such as vegetable oils may be marked to identify the product produced at a particular source, or certified to a particular standard.

One problem which is known to exist with the marking of fuel liquids in particular, is the potential for the tracer to be removed, by evaporation from the fuel, by degradation of the tracer through ageing or exposure to environmental conditions such as heat, sunlight or air or alternatively by deliberate removal of the tracer for unlawful purposes such as for avoidance of tax. Methods for deliberate removal of tracers include adsorption of the tracer onto common adsorbent materials such as charcoal or clays, exposure to radiation, such as ultraviolet light, oxidation etc. A useful fuel tracer therefore needs to be resistant to removal by these common methods and also to more sophisticated treatments such as treatment with acids and/or bases. It is an object of the invention to provide a method of marking hydrocarbon liquids which is more resistant to removal of the tracer than known methods.

WO 2011/032857 describes hydrocarbon markers based on aromatic compounds in which at least two of the substituents are carboxyl groups, i.e. COOR, where R represents H, $C_1$-$C_{20}$ alkyl, $C_2$-$C_{20}$ alkenyl, $C_2$-$C_{20}$ alkynyl, $C_3$-$C_{15}$ cycloalkyl or aryl. We have found that aromatic compounds having carboxyl substituents may be less resistant to removal from hydrocarbons than the compounds used as tracers in the method of the present invention.

According to the invention, a compound of Formula I or Formula II is used as a tracer compound for the marking and identification of hydrocarbon liquids:

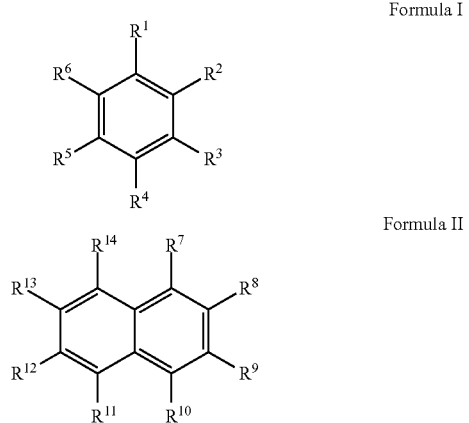

wherein at least one of $R^1$-$R^6$ in Formula I and at least one of $R^7$-$R^{14}$ in Formula II is selected from:
i. a bromine or fluorine atom;
ii. a partially or fully halogenated alkyl group;
iii. a branched or cyclic $C_4$-$C_{20}$ alkyl group;
iv. an aliphatic substituent linking two positions selected from $R^1$-$R^6$ in Formula I to one another or two positions selected from $R^7$-$R^{14}$ in Formula II to one another; or
v. a phenyl group substituted with a halogen atom, an aliphatic group or halogenated aliphatic group and further wherein none of $R^1$-$R^6$ in Formula I and none of $R^7$-$R^{14}$ in Formula II represent a sulphonate group or COOR$^{15}$, where $R^{15}$ represents H, $C_1$-$C_{20}$ alkyl, $C_2$-$C_{20}$ alkenyl, $C_2$-$C_{20}$ alkynyl, $C_3$-$C_{15}$ cycloalkyl or aryl.

We also provide, according to the invention, a method of marking a hydrocarbon liquid comprising the step of adding a compound of Formula I or Formula II as a tracer compound to said liquid and subsequently analysing a sample of a hydrocarbon liquid for the presence of said tracer compound to determine whether said sample is a sample of said marked hydrocarbon liquid.

We also provide, according to the invention, a hydrocarbon liquid containing a tracer compound at a concentration of less than or equal to 500 ppbv, wherein said tracer compound is a compound of Formula I or Formula II:

Formula I
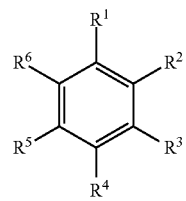

Formula II
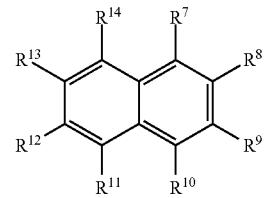

and wherein at least one of $R^1$-$R^6$ in Formula I and at least one of $R^7$-$R^{14}$ in Formula II is selected from:
i. a bromine or fluorine atom;
ii. a partially or fully halogenated alkyl group;
iii. a branched or cyclic $C_4$-$C_{20}$ alkyl group;
iv. an aliphatic substituent linking two positions selected from $R^1$-$R^6$ in Formula I to one another or two positions selected from $R^7$-$R^{14}$ in Formula II to one another; or
v. a phenyl group substituted with a halogen atom, an aliphatic group or halogenated aliphatic group and further wherein none of $R^1$-$R^6$ in Formula I and none of $R^7$-$R^{14}$ in Formula II represent a sulphonate group or COOR$^{15}$, where $R^{15}$ represents H, $C_1$-$C_{20}$ alkyl, $C_2$-$C_{20}$ alkenyl, $C_2$-$C_{20}$ alkynyl, $C_3$-$C_{15}$ cycloalkyl or aryl.

The hydrocarbon liquid may be a pure compound such as hexane or octane or it may comprise a mixture of compounds such as a distillation fraction having a particular range of boiling points. The hydrocarbon liquid may be intended for use as a chemical, a solvent or a fuel. The invention is of particular use for marking liquid hydrocarbon fuels such as gasoline and diesel fuels. Therefore, in a preferred embodiment of the use and method of the invention, the hydrocarbon liquid comprises a diesel fuel, a gasoline fuel or a solvent. In one particular application of the method, a low-tax fuel such as an agricultural diesel may be marked in order to detect any subsequent sale and use for purposes such as road-vehicle fuel which would normally be taxed more highly. In such cases unlawful dilution or substitution of a more highly taxed fuel with the low-taxed fuel may be detected by analysis of the highly taxed fuel to determine whether the tracer is present. Therefore in these cases, it is highly beneficial to use a tracer compound in the low-taxed fuel which is not easily removed, or laundered, from the fuel to a level at which it can no longer be detected. We have found that compounds of Formula I and Formula II are resistant to removal from hydrocarbon fuels by several known methods of fuel laundering.

Preferably, when any of $R^1$-$R^{14}$ is a halogen or halogenated alkyl group, the halogen atom is selected from bromine or fluorine and the halogenated alkyl group is a bromoalkyl or fluoroalkyl group. The halogenated alkyl group(s) may be partially or fully halogenated, linear or branched, acyclic or cyclic aliphatic groups. Preferred halogenated alkyl groups include trifluoromethyl, 1,1-difluoroethyl, fluoroallyl, heptafluoropropyl, tridecafluorohexyl, heptadecafluorooctyl. Most preferably at least two R substituents in either Formula I or II consist of a halogen atom or a halogenated alkyl group.

Alkyl group substituents may be straight chain or branched acyclic or cyclic aliphatic groups, preferably consisting of 4-12 carbon atoms. Branched or cyclic aliphatic groups are preferred. Preferred groups include tert-butyl, 1,1-dimethylpropyl, 2,2-dimethylpropyl (neo-pentyl), 1,1-dimethylbutyl, 1-ethyl-1-methylpropyl, 2,2-dimethylbutyl, 1,1,2-trimethylpropyl, 1,2,2-trimethylpropyl, 1-ethyl-2,2-dimethylpropyl, 1-methylethyl-2,2-dimethylpropyl, 1,1,3,3-tetramethylbutyl, cyclopentyl, cyclohexyl, 2-methylcyclohexyl, 3-methylcyclohexyl, 4-methylcyclohexyl, 2-ethylhexyl, 1-adamantyl, 2-adamantyl and decahydronaphthyl groups. Particularly preferred are substituents including quaternary substituted carbon atoms, such as tertiary butyl. In one preferred embodiment, at least one of $R^1$-$R^{14}$ in Formula I or Formula II comprises an aliphatic or halogenated alkyl substituent containing a quaternary-substituted carbon atom.

It is preferred that none of $R^1$-$R^6$ in Formula I and $R^7$-$R^{14}$ in Formula II include fused aromatic rings such as naphthyl or anthracenyl, saturated heterocycles where the heteroatom is anything other than oxygen, unsaturated heterocycles, amino, imino, N-oxide, nitro, hydroxyl, carboxyl, ester, amide, acetal, thiol, thiol ethers, disulfides, sulfoxide, sulfone, sulfonate, phosphite ester, phosphate ester, cationic, anionic or zwitterionic groups; or metal containing substituents. It is possible, however, to use a molecule containing one of the above unpreferred groups provided that sufficient halogen, halogenated alkyl or bulky alkyl groups of the preferred type are present in the molecule to provide resistance to laundering. Preferably those $R^1$-$R^6$ in Formula I and $R^7$-$R^{14}$ in Formula II which are not selected from a bromine or fluorine atom; a partially or fully halogenated alkyl group; a branched or cyclic $C_4$-$C_{20}$ alkyl group; an aliphatic substituent linking two positions selected from $R^1$-$R^6$ in Formula I to one another or two positions selected from $R^7$-$R^{14}$ in Formula II to one another; or a phenyl group substituted with a halogen atom, an aliphatic group or halogenated aliphatic group are H.

Suitable tracer compounds include 2,3-difluorobromobenzene, 2,4-difluorobromobenzene, 2,5-difluorobromobenzene, 2,6-difluorobromobenzene, 3,5-difluorobromobenzene, 3,5-difluorobenzene, pentafluorobromobenzene, 2,3,5,6-tetrafluorobromobenzene, 1-bromo-2,3,5,6-tetrafluorobenzene 2,3,4-trifluorobromobenzene, 2,3,5-trifluorobromobenzene, 2,3,6-trifluorobromobenzene, 2,4,5-trifluorobromobenzene, 2,4,6-trifluorobromobenzene, 3,4,5-trifluorobromobenzene, 2-(trifluoromethyl)bromobenzene, 3-(trifluoromethyl)bromobenzene, 4-(trifluoromethyl)bromobenzene, 2,4-bis(trifluoromethyl)bromobenzene, 2,5-bis(trifluoromethyl)bromobenzene, 3,5-bis(trifluoromethyl)bromobenzene, 2-fluoro-3-(trifluoromethyl)bromobenzene, 2-fluoro-4-(trifluoromethyl)bromobenzene, 2-fluoro-5-(trifluoromethyl)bromobenzene, 2-fluoro-6-(trifluoromethyl)bromobenzene, 3-fluoro-5-(trifluoromethyl)bromobenzene, 4-fluoro-2-(trifluoromethyl)bromobenzene, 4-fluoro-3-(trifluoromethyl)bromobenzene, 2-methyl-3-(trifluoromethyl)bromobenzene, 2-methyl-5-(trifluoromethyl)bromobenzene and 4-methyl-3-(trifluoromethyl)bromobenzene.

Most preferred tracer compounds have a boiling point greater than 100° C., especially greater than 140° C. at normal atmospheric pressure. A higher boiling compound is more difficult to remove by evaporation techniques including aeration by stirring or sparging air through the marked fuel. Preferably the tracer compound has a boiling point within the distillation range of the hydrocarbon liquid or within 10° C. of the boiling point of the hydrocarbon liquid. Preferably the tracer compound has a boiling point which is within the distillation range of the hydrocarbon liquid to be marked. More preferably, the tracer compound has a boiling point which is within the central 90% of the distillation range of the hydrocarbon liquid to be marked. Diesel has a boiling range from 180-390° C. Gasoline has a boiling range from 25-215° C. When a hydrocarbon liquid which has a boiling range, such as diesel or gasoline, is to be marked, then a tracer compound having a suitable boiling point would be selected based upon the boiling range of the hydrocarbon liquid. When a hydrocarbon solvent or a liquid having a distinct boiling point, such as hexane, is to be marked then the tracer compound is preferably selected to fall within 10 degrees of the boiling point of that hydrocarbon. The tracer compound is a liquid at room temperature or it is a solid which is soluble in the quantities at which it is to be used either in the liquid or in a master-batch formulation.

The tracer compound is added to the hydrocarbon liquid in such an amount as to provide a concentration of the tracer compound which is detectable by readily available laboratory methods capable of identifying the tracer compound in the liquid at the concentrations used. Suitable methods include, but are not limited to, gas chromatography coupled with a suitable detector such as an electron capture detector or a mass spectrometer. The hydrocarbon liquid may be identified as a hydrocarbon liquid containing the tracer by comparing the spectrum or other form of analytical result obtained from analysing the sample with a spectrum or result obtained from analysing a standard sample of a known hydrocarbon liquid containing a known concentration of the tracer. The sample result or a characteristic feature of the result, such as a peak area, may be compared with a value for a corresponding result or characteristic of a standard sample which is held in a memory of a data processing device. Alternatively the result from the sample may be interpreted without referring to a known standard result or sample.

Typically, the concentration of tracer in the hydrocarbon liquid is within the range from 1 ppbv (part per billion by volume) to 100 ppbv, the actual amount used depending on the detection method and limit of detection of the particular tracer compound used. The tracer compound may be present at a higher concentration than 100 ppbv, for example up to 500 ppbv or even up to 1 ppmv (part per million by volume), although when the product to be marked is a high-volume commodity such as a motor-fuel, economic considerations usually favour lower levels of tracer compound. The tracer compound may be supplied in the form of a concentrated dosing solution (or master-batch) of the tracer compound in a solvent. In this case the preferred solvent is a liquid which is similar to the liquid to be marked, although a different solvent, e.g. a hexane or mixed paraffins solvent may be used provided the presence of such a solvent can be tolerated in the hydrocarbon liquid to be marked. The concentrated dosing solution can be added to the hydrocarbon liquid to be marked so as to produce the required final concentration of the tracer compound by dilution. More than one tracer compound may be added to the liquid.

The selected tracer compound(s) is resistant to laundering by adsorption on activated charcoal or clay. In a preferred embodiment, at least 50% (more preferably at least 60%, especially at least 80%) of the tracer compound is retained in the hydrocarbon liquid after a sample of the liquid containing the tracer compound has passed through a column of fresh activated charcoal. The test to be applied for resistance to laundering by adsorption on a solid adsorbent is described below. Preferably at least 50% (more preferably at least 60%, especially at least 80%) of the tracer compound is retained in the hydrocarbon liquid after a sample of the liquid containing the tracer compound has passed through a column of fresh sepiolite clay.

Preferably the selected tracer compound(s) is resistant to laundering by chemical treatment with an acid or a base. In preferred embodiments, at least 50% (more preferably at least 75%) of the tracer compound is retained in the hydrocarbon liquid after a sample of the liquid containing 10-15 ppbv of the tracer compound has been vigorously agitated in contact with 10% aqueous HCl. Preferably at least 50% (more preferably at least 75%) of the tracer compound is retained in the hydrocarbon liquid after a sample of the liquid containing 10-15 ppbv of the tracer compound has been vigorously agitated in contact with 10% aqueous $H_2SO_4$. Preferably at least 50% (more preferably at least 75%) of the tracer compound is retained in the hydrocarbon liquid after a sample of the liquid containing 10-15 ppbv of the tracer compound has been vigorously agitated in contact with 10% aqueous NaOH. Preferably at least 50% (more preferably at least 75%) of the tracer compound is retained in the hydrocarbon liquid after a sample of the liquid containing 10-15 ppbv of the tracer compound has been vigorously agitated in contact with methanolic KOH (3M aqueous KOH diluted 1:10 in methanol). The test procedure for resistance to laundering by these chemical treatments is described below.

The invention will be further described in the following examples. In the Examples, the test methods which are used are described below. The meaning of ppb v/v is parts per billion based on the volume of liquid tracer compound in the total volume of liquid. In the following tests, T1 is pentafluorobromobenzene; T2 is 3-(trifluoromethyl)bromobenzene.

Test For Resistance to Removal By a Solid Adsorbant (charcoal, Clay or Silica Gel)

A 30 cm long chromatography column, having an inside diameter of 1 cm, was filled with the solid adsorbent to a depth of about 15 cm. The adsorbent was supported in the column on a glass frit. 15 ml of a diesel fuel containing 10 ppb v/v of the test tracer compound was added to the column and allowed to percolate through the adsorbent bed under gravity. The liquid eluting from the column was collected, sealed into an autosampler vial and analysed immediately by gas chromatography-mass spectrometry (GCMS). The amount of tracer detected in the collected liquid is reported below in Table 1, as a percentage of the original concentration. Approximately 5 ml of liquid was retained on the column, presumably in the pores and voidage of the adsorbent particle bed.

The adsorbents used were:

Charcoal:—a powdered activated Norit™ charcoal (type RBAA-3) from Fluka (product number 29238), Sepiolitic clay: a pure fine sepiolite clay from RS Minerals Silica gel 60 from Fluka (product number 60738)

Fine powdered $Al_2O_3$ from Sigma Aldrich (product number 11028)

Aluminium hydroxide, fine powder from Sigma Aldrich (product number 23918-6)

Kaolin: fine powder from Sigma Aldrich (product number K7375)

TABLE 1

| Tracer compound | Adsorbent | | | | | |
| --- | --- | --- | --- | --- | --- | --- |
| | Sepiolitic clay | Charcoal | Silica gel | $Al_2O_3$ | $Al(OH)_3$ | Kaolin |
| T1 | 90 | 88 | 94 | 97 | 91 | 100 |
| T2 | 99 | 87 | 92 | 95 | 93 | 98 |

Multi-Pass Adsorbant Test

The above test procedure was carried out using 50 ml of diesel fuel marked with 10 ppb v/v of the tracer compound and the eluted liquid was collected in an open beaker before being passed through a second column packed with fresh adsorbent. The liquid from the second column was collected in an open beaker before being passed through a third column packed with fresh adsorbent. A sample of the liquid collected from each column was taken for analysis by GCMS and the concentration of the tracer in the eluted liquid is shown in Table 2 as a percentage of the original concentration. When the concentration is greater than 100%, it is believed that the diesel fuel was retained on the adsorbent in preference to the tracer so that the solution became more concentrated.

TABLE 2

| Tracer compound | Sepiolitic clay | | | Charcoal | | |
| --- | --- | --- | --- | --- | --- | --- |
| | $1^{st}$ pass | $2^{nd}$ pass | $3^{rd}$ pass | $1^{st}$ pass | $2^{nd}$ pass | $3^{rd}$ pass |
| T1 | 93 | 73 | 53 | 78 | 68 | 41 |
| T2 | 102 | 99 | 94 | 70 | 40 | 18 |

Test for Loss of Tracer Compound on Standing 1 ml of diesel fuel marked with 10 ppb v/v of the test tracer compound was placed in an open topped 2 ml autosampler vial, and repeatedly analysed by GCMS over the course of one day after standing in normal laboratory conditions to determine the concentration of the tracer compound in the diesel. The samples were interspersed with sealed calibration standards to correct for any instrument drift over the period of analysis. The concentration of the tracer in the liquid is shown in Table 3 as a percentage of the original concentration. When the concentration is greater than 100%, it is believed that the diesel fuel evaporated more quickly than the tracer so that the solution became more concentrated.

TABLE 3

| | T1 | T2 |
|---|---|---|
| Concentration of tracer after 24 hours (%) | 97 | 95 |

Test for Stability to Ultra-Violet Radiation 20 mls of diesel fuel marked with 10 ppb v/v of the test tracer compound were placed in each of two headspace vials which were sealed with airtight crimp tops, one of which was exposed to 365 nm UV light, the other left shaded on the laboratory bench. After 24 hours, approximately 0.5 mls was removed from each vial for analysis and crimp caps replaced with new. This was repeated again after 52 hours. Table 4 shows the % of the original concentration of tracer found by GCMS in the treated sample at the time shown.

TABLE 4

| Tracer compound | 0 hrs | 24 hrs | 52 hrs |
|---|---|---|---|
| T1 | 100 | 94.6 | 87 |
| T2 | 100 | 98 | 91.2 |

Test for Resistance to Removal by Chemical Treatment

A quantity of the diesel fuel marked with 13 ppb v/v of the test tracer compound was shaken vigorously with an equal volume of a chemical agent selected from 10% HCl in deionised water, 10% $H_2SO_4$ in deionised water, 10% NaOH in deionised water and methanolic KOH (3M aqueous KOH diluted 1:10 in methanol). The mixture was allowed to settle, then shaken for a further minute before settling again. A sample of the diesel layer was analysed by GCMS and the concentration of the tracer in the treated diesel liquid is shown in Table 5.

TABLE 5

| Tracer compound | 10% HCl | 10% $H_2SO_4$ | 10% NaOH | KOH/MeOH |
|---|---|---|---|---|
| T1 | 78 | 87 | 86 | 85 |
| T2 | 73 | 89 | 88 | 88 |

The invention claimed is:

1. A method of identifying a hydrocarbon liquid comprising the steps of:
adding to said liquid, 1,3,5-tritertbutylbenezne as a tracer compound,

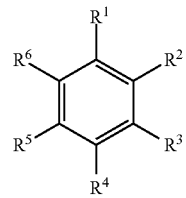

Formula I and
subsequently analysing a sample of a hydrocarbon liquid for the presence of said tracer compound to determine whether said sample is a sample of said marked hydrocarbon liquid.

2. The method according to claim 1, wherein at least 50% of the tracer compound is retained in the hydrocarbon liquid after a sample of the liquid containing from 10 to 15 ppbv of the tracer compound has passed through a column of fresh activated charcoal.

3. The method according to claim 1, wherein at least 50% of the tracer compound is retained in the hydrocarbon liquid after a sample of the liquid containing from 10 to 15 ppbv of the tracer compound has passed through a column of fresh powdered sepiolitic clay.

4. The method according to claim 1, wherein the tracer compound has a boiling point within the distillation range of the hydrocarbon liquid or within 10° C. of the boiling point of the hydrocarbon liquid.

5. The method according to claim 1, wherein more than one tracer compound is added to the hydrocarbon liquid.

6. The method according to claim 1, wherein at least 50% of the tracer compound is retained in the hydrocarbon liquid after a sample of the liquid containing from 10 to 15 ppbv of the tracer compound has been vigorously agitated in contact with 10% aqueous HCl.

7. The method according to claim 1, wherein at least 50% of the tracer compound is retained in the hydrocarbon liquid after a sample of the liquid containing from 10 to 15 ppbv of the tracer compound has been vigorously agitated in contact with 10% aqueous $H_2SO_4$.

8. The method according to claim 1, wherein at least 50% of the tracer compound is retained in the hydrocarbon liquid after a sample of the liquid containing from 10 to 15 ppbv of the tracer compound has been vigorously agitated in contact with 10% aqueous NaOH.

9. The method according to claim 1, wherein at least 50% of the tracer compound is retained in the hydrocarbon liquid after a sample of the liquid containing from 10 to 15 ppbv of the tracer compound has been vigorously agitated in contact with methanolic KOH.

10. A hydrocarbon liquid containing a tracer compound as used in claim 1 at a concentration of from 1 to 500 ppbv.

11. The method according to claim 1, wherein the tracer compound is added to the hydrocarbon liquid in such a quantity as to produce a final concentration in the liquid of from 1 to 500 ppbv.

12. The method according to claim 11, wherein the tracer compound is added to the hydrocarbon liquid in such a quantity as to produce a final concentration in the liquid in the range from 1-100 ppbv.

* * * * *